United States Patent
Negiz et al.

(10) Patent No.: US 7,816,571 B2
(45) Date of Patent: Oct. 19, 2010

(54) SELECTIVE HYDROGENATION PROCESS USING LAYERED CATALYST COMPOSITION

(75) Inventors: Antoine Negiz, Wilmette, IL (US); Gregory J. Gajda, Mount Prospect, IL (US)

(73) Assignee: UOP LLC, Des Plaines, IL (US)

(*) Notice: Subject to any disclaimer, the term of this patent is extended or adjusted under 35 U.S.C. 154(b) by 328 days.

(21) Appl. No.: 11/954,020

(22) Filed: Dec. 11, 2007

(65) Prior Publication Data

US 2008/0146855 A1  Jun. 19, 2008

Related U.S. Application Data

(60) Provisional application No. 60/870,265, filed on Dec. 15, 2006.

(51) Int. Cl.
*C07C 5/05* (2006.01)
(52) U.S. Cl. .............. 585/260; 585/258; 585/259; 585/273; 585/275; 502/326; 502/332
(58) Field of Classification Search ........... 585/273, 585/275, 259, 260, 258; 502/277, 326, 332
See application file for complete search history.

(56) References Cited

U.S. PATENT DOCUMENTS

| | | | | |
|---|---|---|---|---|
| 2,620,314 A | 12/1952 | Hoekstra | ............... | 252/448 |
| 3,145,183 A | 8/1964 | Fisher | ............... | 252/477 |
| 3,274,124 A | 9/1966 | O'Hara | ............... | 252/451 |
| 3,909,450 A | 9/1975 | O'Hara | ............... | 252/438 |
| 3,951,860 A | 4/1976 | Acres et al. | ............... | 252/432 |
| 4,077,912 A | 3/1978 | Dolhyj et al. | ............... | 252/461 |
| 4,255,253 A | 3/1981 | Herrington et al. | ..... | 208/216 PP |
| 4,440,871 A | 4/1984 | Lok et al. | ............... | 502/214 |
| 4,567,029 A | 1/1986 | Wilson et al. | ............... | 423/306 |
| 4,786,625 A | 11/1988 | Imai et al. | ............... | 502/326 |
| 4,793,984 A | 12/1988 | Lok et al. | ............... | 423/306 |
| 4,988,659 A | 1/1991 | Pecoraro | ............... | 502/235 |
| 5,276,231 A | 1/1994 | Kocal et al. | ............... | 585/323 |
| 5,516,740 A | 5/1996 | Cody et al. | ............... | 502/204 |

(Continued)

FOREIGN PATENT DOCUMENTS

JP  54157507 A  12/1979

(Continued)

OTHER PUBLICATIONS

Routschka, et. al. "Refractory Ceramics," in Ullmann's Encyclopedia of Industrial Chemistry, Wiley-VCH, 2002, posted on-line Jun. 15, 2000.*

(Continued)

*Primary Examiner*—In Suk Bullock
*Assistant Examiner*—Bradley Etherton
(74) *Attorney, Agent, or Firm*—Kurt D Van Tassel

(57) ABSTRACT

The use of a layered catalyst composition to selectively hydrogenate $C_5$-$C_{11}$ diolefins in a hydrocarbon mixture to one or more respective $C_5$-$C_{11}$ monoolefins is disclosed. The layered catalyst comprises an inner core having a first inorganic oxide and an outer layer bonded to the inner core. The outer layer has a non-refractory second inorganic oxide with at least one Group 1-2 metal and at least one Group 8-10 metal dispersed thereon.

18 Claims, 6 Drawing Sheets

U.S. PATENT DOCUMENTS

| | | | |
|---|---|---|---|
| 5,866,735 A * | 2/1999 | Cheung et al. | 585/273 |
| 6,127,310 A * | 10/2000 | Brown et al. | 502/339 |
| 6,177,381 B1 | 1/2001 | Jensen et al. | 502/325 |
| 6,280,608 B1 * | 8/2001 | Jensen et al. | 208/143 |
| 6,486,370 B1 | 11/2002 | Rende et al. | 585/444 |
| 6,670,516 B1 | 12/2003 | Marinangeli et al. | 585/323 |
| 6,756,340 B2 | 6/2004 | Voskoboynikov et al. | 502/328 |
| 6,794,552 B2 * | 9/2004 | Cheung et al. | 585/259 |
| 7,453,016 B1 | 11/2008 | Gajda | |
| 7,534,737 B2 | 5/2009 | Gajda | |
| 2003/0036476 A1 | 2/2003 | Arnold et al. | 502/325 |
| 2005/0113615 A1 * | 5/2005 | Lowe et al. | 585/259 |
| 2006/0266673 A1 | 11/2006 | Rende et al. | 208/120.1 |
| 2006/0270865 A1 | 11/2006 | Wang et al. | 554/174 |
| 2008/0176737 A1 | 7/2008 | Negiz et al. | |

FOREIGN PATENT DOCUMENTS

| | | |
|---|---|---|
| WO | WO 98/14274 | 4/1998 |

OTHER PUBLICATIONS

R. K. Iler, Chemistry of Silica: Solubility, Polymerization, Colloid and Surface Properties and Biochemistry, John Wiley & Sons, 1979, pp. 539-544, on-line version available at http://knovel.com.*

* cited by examiner under an oxygen atmosphere diolefins are unstable. Diolefins present a challenge for processes involving catalysts because the diolefins are very reactive and polymerize even under hydrogen atmospheres at high temperatures forming gum. Because of the reactivity of diolefins catalysts that have poor activity are restricted in cycle length and have a propensity for polymerization because of the requirement for high temperatures. It is generally accepted at temperatures about 170° C. (338° F.) excess polymerization causes pressure drops across a catalytic reactor. These problems are generally worse if the catalyst comprises a porous active base such as gamma or theta alumina where polymerization of diolefins can cause swelling of the porous catalyst and can damage the structure of the catalyst.

SELECTIVE HYDROGENATION PROCESS USING LAYERED CATALYST COMPOSITION

CROSS REFERENCE TO RELATED APPLICATION

This application claims the benefit of U.S. Provisional Application No. 60/870,265, filed Dec. 15, 2006.

FIELD OF THE INVENTION

The invention relates to the selective hydrogenation of hydrocarbons. More specifically, the invention relates to the use of a catalyst to selectively hydrogenate $C_5$-$C_{11}$ diolefins in a hydrocarbon mixture to one or more respective $C_5$-$C_{11}$ monoolefins.

BACKGROUND OF THE INVENTION

Hydrocarbon stream feeds like pyrolysis gas feeds can have diene values ranging from 1-120 and diolefin weight percentages in such streams can range from 0.5 weight percent to 50 weight percent or above. Under an oxygen atmosphere diolefins are unstable. Diolefins present a challenge for processes involving catalysts because the diolefins are very reactive and polymerize even under hydrogen atmospheres at high temperatures forming gum. Because of the reactivity of diolefins catalysts that have poor activity are restricted in cycle length and have a propensity for polymerization because of the requirement for high temperatures. It is generally accepted at temperatures about 170° C. (338° F.) excess polymerization causes pressure drops across a catalytic reactor. These problems are generally worse if the catalyst comprises a porous active base such as gamma or theta alumina where polymerization of diolefins can cause swelling of the porous catalyst and can damage the structure of the catalyst.

In situations where the catalyst is an active catalyst there is a tendency for the active catalysts to convert diolefins as well as the monoolefins rapidly and often more selectively to their corresponding paraffins and naphthenes causing excess heat generation. Again, these conditions tend to favor gum formation and this is particularly so in a commercial application where a fixed bed adiabatic reactor is subjected to high temperature rises. The reactor's practical operating window is limited because of the pressure drop problems.

The present invention relates to the use of a layered catalyst to selectively hydrogenate $C_5$-$C_{11}$ diolefins to $C_5$-$C_{11}$ monoolefins, which helps to mitigate some of the above mentioned limitations. The layered catalyst composition comprises an IUPAC Group 1-2 metal and an IUPAC Group 8-10 metal on a layered composition support. The support comprises an inner core of an inorganic oxide, which is preferably a refractory inorganic oxide, such as, without limitation, cordierite, and an outer layer of a non-refractory inorganic oxide, such as, without limitation, gamma alumina.

The current industrial practice for selectively hydrogenating diolefins or unsaturated hydrocarbon fractions is based on the use of sulfided nickel catalysts operating at moderately high temperatures of approximately 185° C. (365° F.). Sulfur loss from the catalyst to the product occurs and sulfur must be replenished to keep the catalyst active and operating optimally. Furthermore, once the sulfur is lost into the product, in some instances the sulfur must also be removed from the product and this adds another level of processing.

Other types of selective hydrogenation processes are also known, such as that described in JP54157507A. JP54157507A describes the use of a palladium catalyst on an alumina support to selectively hydrogenate acetylene and methyl acetylene (alkynes) that are present in olefin fractions obtained in petrochemical processes. The catalyst described in JP54157507A comprises a thin alumina coating over an alpha alumina carrier of spherical or cylindrical shape and being around 1-20 mm in size, length and diameter. The alumina precursor, which can be aluminum nitrate, aluminum chloride, aluminum hydroxide and the like, is coated onto the alpha alumina carrier and then the coated alpha alumina carrier and alumina precursor is heat treated at between 400° C. (752° F.) to 700° C. (1292° F.) to create a thin alumina coating over the alpha alumina carrier. A palladium compound such as palladium chloride, palladium nitrate, and the like is dissolved in a suitable solvent, and then applied to the alumina coating to give effectively an enriched surface coating containing palladium. JP54157507A describes the use of the resulting catalyst in the selective hydrogenation of acetylene in a composition comprising ethylene.

The process disclosed herein has been developed to enable one to selectively hydrogenate $C_5$-$C_{11}$ diolefins to $C_5$-$C_{11}$ monoolefins at relatively high space velocities using a layered catalyst that eliminates the need to use a sulfided nickel catalyst for associated sulfur addition (and in some instances the subsequent removal of sulfur from the product).

US 2003/0036476 A1 describes a coated catalyst having a core and a shell surrounding the core, the core is made up of an inert support material. The shell is made up of a porous support substance, and the shell is physically attached to the core. A catalytically active metal selected from the group consisting of the metals of the 10th and 11th groups of the Periodic Table of the Elements is present in finely divided form in the shell. The coated catalyst is described as being suitable for the selective reduction of unsaturated hydrocarbons, specifically lower $C_2$-$C_4$ unsaturated hydrocarbons.

U.S. Pat. No. 6,177,381 B1, which is incorporated by reference in its entirety, describes a layered catalyst composition showing improved durability and selectivity for dehydrogenating hydrocarbons, a process for preparing the catalyst and processes for using the composition. The catalyst composition comprises an inner core such as alpha-alumina, and an outer layer bonded to the inner core composed of an outer non-refractory inorganic oxide such as gamma-alumina. The outer layer has uniformly dispersed thereon a platinum group metal such as platinum and a promoter metal such as tin. The composition also contains a modifier metal such as lithium. The catalyst composition is prepared by using an organic binding agent such as polyvinyl alcohol which increases the bond between the outer layer and the inner core. The catalyst composition is described as also being suitable for use in dehydrogenation and hydrogenation processes. Likewise, U.S. Pat. No. 6,280,608 B1 also describes a layered catalyst suitable for use in dehydrogenation and hydrogenation processes, while U.S. Pat. No. 6,486,370 B1 is directed to a layered catalyst suitable for use in dehydrogenation processes.

US 2006/0266673 A1 and US 2006/0270865 A1 describe a similar layered catalyst, but with an additional fibrous component in the outer layer. The fiber-containing layered catalyst is described as being suitable for use in dehydrogenation and hydrogenation processes including selective hydrogenation of dienes and trienes.

BRIEF SUMMARY OF THE INVENTION

The process disclosed herein uses a layered catalyst for the treatment of a hydrocarbon stream containing a mixture of at least $C_5$-$C_{11}$ diolefins and $C_5$-$C_{11}$ monoolefins. The process and catalyst are employed to selectively hydrogenate $C_5$-$C_{11}$ diolefins to $C_5$-$C_{11}$ monoolefins at relatively high space velocities and without hydrogenating substantially the $C_5$-$C_{11}$ monoolefins originally present in the mixture.

In one aspect the present invention provides a process for selectively hydrogenating one or more $C_5$-$C_{11}$ diolefins in a hydrocarbon mixture to one or more respective $C_5$-$C_{11}$ monoolefins the process comprising the step of:
(i) bringing the hydrocarbon mixture under selective hydrogenation conditions into contact with a layered catalyst to give substantially a $C_5$-$C_{11}$ monoolefin product;
wherein the layered catalyst comprises:
(a) an inner core comprising a first inorganic oxide, and
(b) an outer layer bonded to said inner core, said outer layer comprising a second inorganic oxide that is non-refractory and has dispersed thereon at least one IUPAC Group 1-2 metal and at least one IUPAC Group 8-10 metal.

The embodiments and objects of the invention will become clearer after the following detailed description.

DETAILED DESCRIPTION OF THE INVENTION

Figure 1:
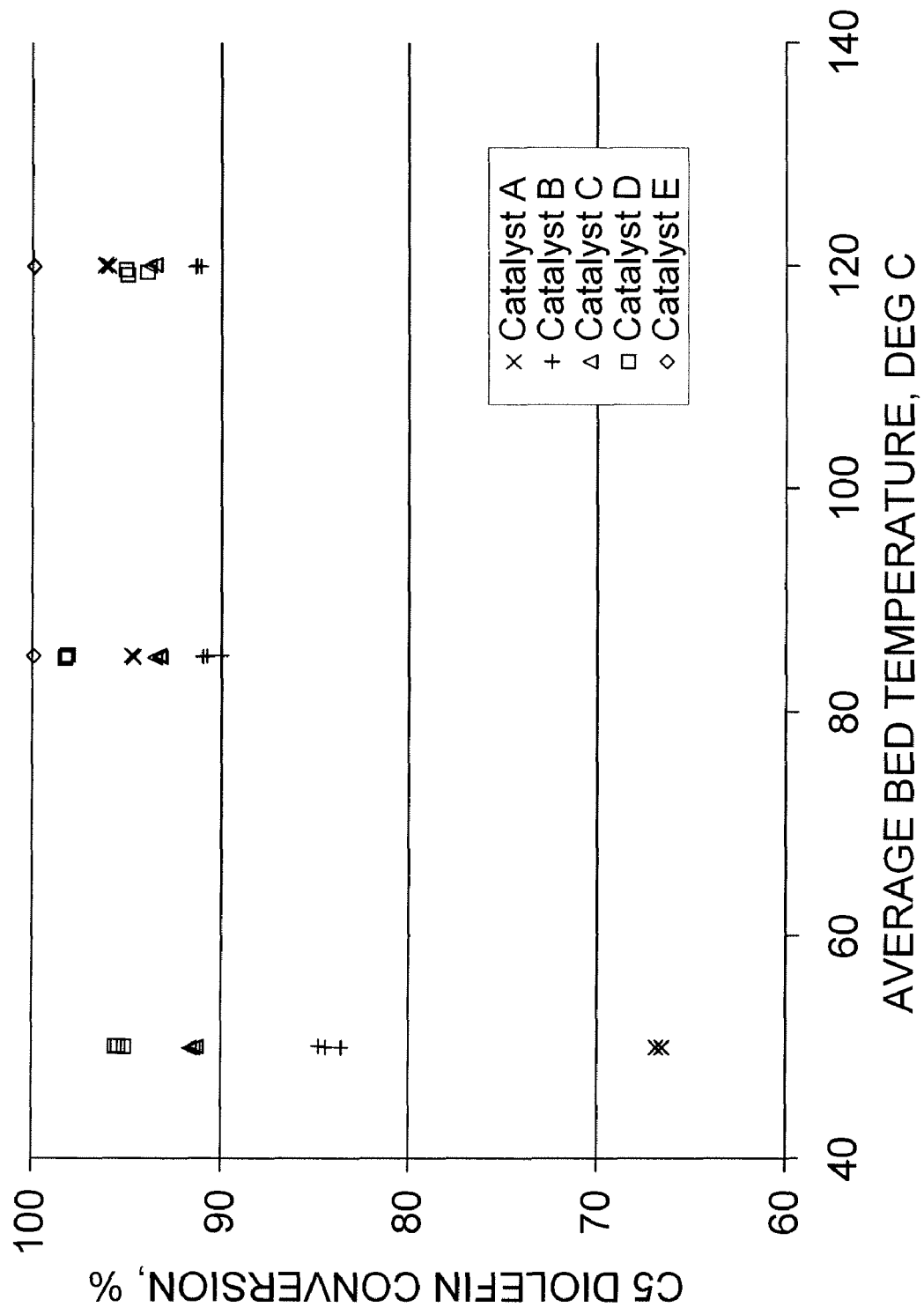
FIG. 1 compares the activities of different catalysts A, B, C, D and E in a plot of the percentage conversion of $C_5$ diolefin against the average bed temperature of the catalyst bed.

As stated, a selective hydrogenation process is disclosed herein.

The selective hydrogenation process is believed to be capable of operating at relatively higher space velocities for a given reaction temperature and equilibrium conversion of diunsaturates than prior processes. Without limiting this invention to any particular theory, it is believed the layered catalyst composition used in the selective hydrogenation process disclosed herein has less restrictions to diffusion of reactants and products in comparison to previous catalysts. Consequently, it is expected that the temperature required to attain a specified equilibrium conversion would be lower and also that at a given conversion higher space velocities could be attained without excessive reactor temperature. Therefore, less catalyst and a smaller reactor would be needed, which would result in reduction in the capital cost of the process.

Specifically, the process disclosed herein relates to the selective hydrogenation of $C_5$-$C_{11}$ diolefins in a mixture of $C_5$-$C_{11}$ monoolefins. The $C_5$-$C_{11}$ diolefins are selectively hydrogenated to the corresponding $C_5$-$C_{11}$ monoolefins without hydrogenation of the original $C_5$-$C_{11}$ monoolefins. The selective hydrogenation occurs when the hydrocarbon mixture comprising $C_5$-$C_{11}$ diolefins and $C_5$-$C_{11}$ monoolefins is brought into contact with a layered catalyst of the invention under selective hydrogenation conditions. Preferred selective hydrogenation conditions for example, without limitation include pressures of about 0 kPa(g) (0 psi(g)) to about 6894 kpa(g) (1000 psi(g)), temperatures of between 30° C. (86° F.) and 300° C. (572° F.), $H_2$ to diolefin mole ratios of about 0.1:1 to about 10:1, preferably about 1.1:1 to about 1.5:1 and/or a hydrogen to total liquid feed molar ratio of about 0.1:1 to 20:1 and liquid hourly space velocities (LHSV) of about 0.5 to about 30 $hr^{-1}$.

The layered catalyst composition comprises an inner core composed of an inorganic oxide, which has substantially lower adsorptive capacity for catalytic metal precursors relative to the outer layer. Preferably, the inner core is a refractory inorganic oxide, but can be non-refractory. Examples of refractory and non-refractory inorganic oxides suitable for the inner core include without limitation alpha alumina, theta alumina, silicon carbide, metals, cordierite, zirconia, titania and mixtures thereof. A preferred refractory inorganic oxide for the inner core is cordierite.

The inner core can be formed into a variety of shapes such as pellets, extrudates, spheres or irregularly shaped particles. It is recognized, however, that not all materials can be formed into any shape. Preparation of the inner core can be done by means known in the art such as oil dropping, pressure molding, metal forming, pelletizing, granulation, extrusion, rolling methods and marumerizing. A spherical or cylindrical inner core is preferred. Once the inner core is prepared, it is calcined at a temperature of about 400° C. (752° C.) to about 1500° C. (2732° F.).

The inner core is then coated with an outer layer of a non-refractory inorganic oxide which is the same or different from the inorganic oxide which may be used as the inner core. Examples of non-refractory inorganic oxides suitable for the outer layer include without limitation theta alumina, silicon carbide, metals, zirconia, titania, gamma alumina, delta alumina, eta alumina, silica/alumina, zeolites, non-zeolitic molecular sieves (NZMS), hydrotalcite and mixtures thereof. This outer layer of non-refractory oxide is one which has a relatively high surface area of between about 50 and 200 $m^2/g$ based on the weight of the outer layer. The outer layer thickness is between about 1 and about 300 micron, preferably between about 25 and about 300 micron, and more preferably between about 25 and about 100 micron. The outer layer has a number of pores distributed across its surface. The pores in the outer layer of the catalyst will preferably have an average pore radius of between 65 to 75 Angstrom. The pore radius size distribution will however, vary from approximately 20 to 250 Angstrom. The pore volume is substantially proportional to the thickness of the outer layer and the average radius of the pores. Where the outer layer is approximately 100 micron thick, the total pore volume will be approximately 0.10 to 0.15 cc/g. Where the outer layer is approximately 200 micron thick, the total pore volume will be approximately 0.20 to 0.30 cc/g. The surface area of a catalyst having a 100 micron thick outer layer will be approximately 35 $m^2/g$, while the surface area of a catalyst having a 200 micron thick outer layer will be approximately 65 $m^2/g$, based on the weight of the catalyst.

It should be pointed out that silica/alumina is not a physical mixture of silica and alumina but means an acidic and amorphous material that has been cogelled or coprecipitated. This term is well known in the art, see e.g., U.S. Pat. Nos. 3,909, 450; 3,274,124; and 4,988,659, all of which are incorporated by reference in their entireties. Examples of zeolites include, but are not limited to, zeolite Y, zeolite X, zeolite L, zeolite beta, ferrierite, MFI, mordenite and erionite. Non-zeolitic molecular sieves (NZMS) are those molecular sieves which contain elements other than aluminum and silicon and include silicoaluminophosphates (SAPOs) described in U.S. Pat. No. 4,440,871, ELAPOs described in U.S. Pat. No. 4,793,984, MeAPOs described in U.S. Pat. No. 4,567,029 all of which are incorporated by reference in their entireties. A preferred inorganic oxide for the outer layer is gamma alumina.

A preferred way of preparing a gamma alumina is by the well-known oil drop method which is described in U.S. Pat. No. 2,620,314, which is incorporated by reference in its entirety. The oil drop method comprises forming an aluminum hydrosol by any of the techniques taught in the art and preferably by reacting aluminum metal with hydrochloric acid; combining the hydrosol with a suitable gelling agent, e.g., hexamethylenetetraamine; and dropping the resultant mixture into an oil bath maintained at elevated temperatures (about 93° C. (199° F.)). The droplets of the mixture remain in the oil bath until they set and form hydrogel spheres. The spheres are then continuously withdrawn from the oil bath and typically subjected to specific aging and drying treatments in oil and ammoniacal solutions to further improve their physical characteristics. The resulting aged and gelled spheres are then washed and dried at a relatively low temperature of about 80° C. (176° F.) to 260° C. (500° F.) and then calcined at a temperature of about 455° C. (851° F.) to 705° C. (1301° F.) for a period of about 1 to about 20 hr. This treatment effects conversion of the hydrogel to the corresponding crystalline gamma alumina.

The layer is applied by forming a slurry of the outer non-refractory oxide and then coating the inner core with the slurry by means well known in the art. Slurries of inorganic oxides can be prepared by means well known in the art which usually involve the use of a peptizing agent. For example, any of the transitional aluminas can be mixed with water and an acid such as nitric, hydrochloric, or sulfuric to give a slurry. Alternatively, an aluminum sol can be made by for example, dissolving aluminum metal in hydrochloric acid and then mixing the aluminum sol with the alumina powder.

The slurry can also contain an organic bonding agent which aids in the adhesion of the layer material to the inner core. Examples of this organic bonding agent include but are not limited to polyvinyl alcohol (PVA), hydroxy propyl cellulose, methyl cellulose and carboxy methyl cellulose. The amount of organic bonding agent which is added to the slurry will vary considerably from about 0.1 wt-% to about 3 wt-% of the slurry. How strongly the outer layer is bonded to the inner core can be measured by the amount of layer material lost during an attrition test, i.e., attrition loss. Loss of the outer layer by attrition is measured by agitating the catalyst, collecting the fines and calculating an attrition loss, in the manner described in Example 11 in U.S. Pat. No. 6,177,381 B1. It has been found that by using an organic bonding agent as described above, the attrition loss is less than about 10 wt-% of the outer layer.

Depending on the particle size of the outer inorganic oxide, it may be necessary to mill the slurry in order to reduce the particle size and simultaneously give a narrower particle size distribution. This can be done by means known in the art such as ball milling for times of about 30 min to about 5 hr and preferably from about 1.5 to about 3 hr. It has been found that using a slurry with a narrow particle size distribution improves the bonding of the outer layer to the inner core.

Without wishing to be bound to any particular theory, it appears that bonding agents such as PVA aid in making an interlocking bond between the outer layer material and the inner core. Whether this occurs by the PVA reducing the surface tension of the core or by some other mechanism is not clear. What is clear is that a considerable reduction in loss of the outer layer by attrition is observed.

The slurry may also contain an inorganic bonding agent selected from an alumina bonding agent, a silica bonding agent or mixtures thereof. Examples of silica bonding agents include silica sol and silica gel, while examples of alumina bonding agents include alumina sol, boehmite and aluminum nitrate. The inorganic bonding agents are converted to alumina or silica in the finished composition. The amount of inorganic bonding agent varies from about 2 to about 15 wt-% as the oxide, and based on the weight of the slurry.

The slurry can also contain a modifier metal selected from the group consisting of alkali metals, alkaline earth metals and mixtures thereof. The alkali and alkaline earth metals which can be used as modifier metals in the practice of this invention include lithium, sodium, potassium, cesium, rubidium, beryllium, magnesium, calcium, strontium and barium. Preferred modifier metals are lithium, potassium, sodium and cesium with lithium and sodium being especially preferred. One method involves preparing the slurry with a solution (preferably aqueous) of a decomposable compound of the modifier metal or modifier metal precursor. By decomposable is meant that upon heating the metal compound is converted to the metal or metal oxide with the release of byproducts. Illustrative of the decomposable compounds of the alkali and alkaline earth metals are the halide, nitrate, carbonate or hydroxide compounds, e.g., potassium hydroxide, lithium nitrate.

Coating of the inner core with the slurry can be accomplished by means such as rolling, dipping, spraying, etc. One preferred technique involves using a fixed fluidized bed of inner core particles and spraying the slurry into the bed to coat the particles evenly. The thickness of the layer can vary considerably, but usually is from about 1 to about 300 micron preferably from about 25 to about 300 micron, and more preferably from about 25 to about 100 micron. It should be pointed out that the optimum layer thickness depends on the use for the catalyst and the choice of the outer inorganic oxide. Once the inner core is coated with the layer of outer inorganic oxide, the resultant layered support is dried at a temperature of about 100° C. (212° F.) to about 320° C. (608° F.) for a time of about 1 to about 24 hr and then calcined at a temperature of about 400° C. (752° F.) to about 900° C. (1652° F.) for a time of about 0.5 to about 10 hr to effectively bond the outer layer to the inner core and provide a layered catalyst support. Of course, the drying and calcining steps can be combined into one step.

Having obtained the layered catalyst support, the catalytic metals and/or metal precursors can be dispersed on the layered support by means known in the art. Thus, at least one IUPAC Group 1-2 metal/metal precursor and at least one IUPAC Group 8-10 metal/metal precursor can be dispersed on the outer layer. The IUPAC Group 1-2 metal and/or metal precursor includes without limitation lithium, sodium, potassium, cesium, rubidium, beryllium, magnesium, calcium, strontium and barium. The IUPAC Group 8-10 metal and/or metal precursor includes platinum, palladium, rhodium, iridium, ruthenium and osmium.

The catalytic metals can be deposited on the layered support in any suitable manner known in the art. One method involves impregnating the layered support with a solution (preferably aqueous) of a decomposable compound of the metals or metal precursors. Illustrative of the decomposable compounds of the IUPAC Group 1-2 metals are lithium nitrate, sodium carbonate, potassium nitrate, magnesium chloride and calcium nitrate illustrative of the decomposable compounds of the IUPAC Group 8-10 metals are palladium nitrate, chloroplatinic acid, nickel chloride, rhodium chloride The catalyst also preferably contains at least one element component from IUPAC Groups 11-17, including but not limited to sulfur and the metals copper, silver, gold, tin, germanium and lead. Without being bound to any particular theory, it is believed that on the catalyst the IUPAC Group 8-10 metal is primarily catalytically active, the IUPAC Group 1-2 metal is a promoter metal, and the optional IUPAC Group 11-17 element is a modifier.

All of the metals can be impregnated into the outer layer using one common solution or they can be sequentially impregnated in any order, but not necessarily with equivalent results. A preferred impregnation procedure involves the use of a steam-jacketed rotary dryer. The catalyst support is immersed in the impregnating solution containing the desired metal compound contained in the dryer and the support is tumbled therein by the rotating motion of the dryer. The catalyst support is in the presence of a liquid phase, and preferably in an all-liquid phase. The impregnating solution is present in an excess relative to the amount of catalyst support so that free liquid is present. Precipitation of the metals is prevented by proper control of the pH of the impregnating solution. Evaporation of the solution in contact with the tumbling support is expedited by applying steam to the dryer jacket. The resultant composite is allowed to dry under any suitable conditions, such as ambient temperature conditions or at a temperature of about 80° C. (176° F.) to about 110° C. (230° F.), followed by calcination at a temperature of about 400° C. (752° F.) to about 700° C. (1292° F.) for a time of about 1 to about 4 hr, thereby converting the metal compound to the metal or metal oxide.

In one method of preparation the method involves adding one or more of the metal components to the outer inorganic oxide prior to applying it as a layer onto the inner core. For example, either the IUPAC Group 1-2 or Group 8-10 metals or both can be added to the slurry. Thus, in one method, the catalytic metals are deposited onto the outer inorganic oxide prior to depositing it as a layer onto the inner core. The catalytic metals can be deposited onto the outer refractory oxide powder in any order although not necessarily with equivalent results.

As a final step in the preparation of the layered catalyst composition, the catalyst composition is reduced under hydrogen or other reducing atmosphere in order to ensure that the IUPAC Group 8-10 metal components are in the metallic state (zero valent). Reduction is carried out at a temperature of about 100° C. (212° F.) to about 650° C. (1202° F.) for a time of about 0.5 to about 10 hr in a reducing environment, preferably dry hydrogen.

As an optional step in the preparation of the layered catalyst composition, the layered catalyst composition may be treated hydrothermally. Hydrothermal treatment processes are generally known to those skilled in the art for modifying the physical characteristics of non-refractory oxides. However, a number of these conventional hydrothermal treatment processes can be applied to modifying the physical characteristics of layered sphere catalyst compositions as disclosed herein. For example, hydrothermal treatment comprises subjecting the layered catalyst composition to conditions comprising the presence of water, a temperature of from 100° C. (212° F.) to 1200° C. (2192° F.), and a pressure of from 0 kPa(g) (0 psi(g)) to 10133 kpa(g) (1470 psi(g)). During the hydrothermal treatment, the layered catalyst composition may be contacted with a liquid or vapor stream containing water at a concentration of from slightly above 0 vol-%, e.g. 50 vol-ppm, to 100 vol-% water. The duration of the hydrothermal treatment may be from as little as 1 minute up to 10 or 20 hours, even 1 or more days. In one hydrothermal treatment, the layered catalyst composition is placed in an autoclave, the layered catalyst composition is then completely covered by a water-containing liquid which is preferably liquid water, next the autoclave is closed and placed in an oven, and the oven is then maintained at a temperature of about 200° C. (392° F.) for a period of time of up to from 8 to 10 hours. In another hydrothermal treatment, the layered catalyst composition is placed in an oven or furnace, a gas is passed through the oven or furnace, and the oven is then maintained at a temperature of from 260° C. (500° F.) to 816° C. (1500° F.) for a period of time of from 1 to 24 hours. In this hydrothermal treatment, water may be carried by the flowing gas across the layered catalyst composition, water may be present in or on the layered catalyst composition prior to its being heated in the oven or furnace, or both. The gas may be any suitable gas, such as a gas comprising air, oxygen, nitrogen, an inert gaseous component, or mixtures thereof.

The optional hydrothermal treatment may be performed prior to or after dispersing the catalytic metals and/or metal precursors on the layered support, prior to or after calcining the layered support, or prior to or after reducing the catalyst composition. Hydrothermally treating at different steps during the preparation of the layered catalyst composition may not give equivalent results. As optional steps after the hydrothermal treatment, the hydrothermally treated material may be allowed to dry and then may be calcined as described above. If the hydrothermal treatment is done after dispersing the catalytic metals and/or metal precursors on the layered support, the hydrothermal treatment and any subsequent thermal treatments are preferably performed prior to reducing the catalyst composition. If the hydrothermal treatment is done after reducing the catalyst composition, an additional optional reduction step may be performed. Without being bound to any particular theory, it is believed that hydrothermal treatment modifies the pore size distribution of the layered catalyst composition, modifies the size of the metal clusters on the layered catalyst composition if the catalytic metals and/or metal precursors have been dispersed on the layered support prior to the hydrothermal treatment, or modifies both. It is believed that such modifications affect the performance, especially conversion and selectivity, of the layered catalyst composition.

In the preferred embodiments the metals are uniformly distributed throughout the outer layer of outer inorganic oxide and are substantially present only in the outer layer. It is also preferred that the IUPAC Group metals be distributed uniformly through the outer layer. Preferably the ratio of the IUPAC Group 1-2 to the IUPAC Group 8-10 metals over the outer layer of the inorganic oxide is substantially constant.

The shape and size of the catalyst particles depends on a number of technical and economic factors and considerations, such as the allowable pressure drop across the selective hydrogenation reactor, the amount of catalyst and the cost of production. The preferred shape of the particle is spherical. It is preferred that the catalyst particle has a diameter of about 0.8 mm (1/32 in.) to 6.4 mm (1/4 in.), preferably about 1.6 mm or 1600 micron (1/16 in.).

The hydrogenatable hydrocarbon mixtures used in the selective hydrogenation process disclosed herein contain a diunsaturate, preferably a diolefin, and a monounsaturate, preferably a monoolefin. Any unsaturates in the hydrogenatable hydrocarbon mixture are preferably aliphatic olefins having from about 5 to 11 carbon atoms per molecule. In the monoolefin the positioning of the olefinic bond is not critical to the selective hydrogenation process disclosed herein. Conjugated diolefins, however, are more readily selectively hydrogenated to monoolefins than are nonconjugated diolefins. The position of the olefinic bond in the monoolefin is not critical when the monoolefin is used in the manufacture of alkylbenzene detergent precursors as most alkylation catalysts have been found to promote migration of the olefinic bond. The branching of the hydrocarbon backbones of the monoolefin and the diolefin are not critical to the selective hydrogenation process disclosed herein. However, the branching of the hydrocarbon backbone of the monoolefin is often more of a concern as the structural configuration of the alkyl group on the alkylbenzene product can affect detergent performance and biodegradability. The olefin, be it the monoolefin or the diolefin, may be unbranched or lightly branched, which as used herein, refers to an olefin having three or four primary carbon atoms and for which none of the remaining carbon atoms are quaternary carbon atoms. A primary carbon atom is a carbon atom which, although perhaps bonded also to other atoms besides carbon, is bonded to only one carbon atom. A quaternary carbon atom is a carbon atom that is bonded to four other carbon atoms.

The aliphatic monoolefin is usually a mixture of two or more monoolefins, and the aliphatic diolefin is usually a mixture of two or more diolefins. For commercial processes, other components may be present with the olefin-containing aliphatic compounds. For instance, the monoolefin and the diolefin may be obtained by the dehydrogenation of a paraffinic feedstock and undehydrogenated paraffin, which is difficult to separate from the olefins, is passed to the selective hydrogenation reactor. The unreacted paraffin may be one or more normal or branched paraffins having from about 5 to 11 carbon atoms per molecule. See, for instance, U.S. Pat. No. 6,670,516 B1, herein incorporated by reference. Generally, where olefin is obtained by the dehydrogenation of a paraffinic feedstock, the molar ratio of olefin to paraffin is between about 1:12 to 1:8; however, such amounts of paraffin are not critical to the processes of this invention. Indeed, olefin-containing feedstocks having an essential absence of paraffins are suitable.

The concentrations of monoolefins and diolefins in the hydrogenatable hydrocarbon mixtures are not critical to the selective hydrogenation process disclosed herein. The mixture can contain from about 0.5 to about 95 mol-% monoolefins and from about 0.1 to about 50 mol-% or higher diolefins. The concentration of diolefins in the hydrogenatable hydrocarbon mixtures is not critical to the selective hydrogenation process disclosed herein. A suitable mixture produced by the dehydrogenation of a paraffinic feedstock usually contains from about 10 to about 15 mol-% monoolefins and from about 0.5 to about 1.5 mol-% diolefins. The molar ratio of monoolefins to diolefin in the mixture is typically from about 50:1 to about 5:1, preferably about 25:1 to about 7:1.

The source of the paraffinic feedstock for dehydrogenation is not critical although certain sources of paraffinic feedstocks will likely result in certain impurities being present. Conventionally, kerosene fractions produced in petroleum refineries either by crude oil fractionation or by conversion processes therefor form suitable feed mixture precursors. Fractions recovered from crude oil by fractionation will typically require hydrotreating for removal of sulfur and/or nitrogen prior to being fed to the subject process. The boiling point range of the kerosene fraction can be adjusted by prefractionation to adjust the carbon number range of the paraffins. In an extreme case the boiling point range can be limited such that only paraffins of a single carbon number predominate. Kerosene fractions contain a very large number of different hydrocarbons and the feed mixture to the subject process can therefore contain 200 or more different compounds. Alternative feedstocks include other petroleum fractions, especially naphtha range fractions.

The paraffinic feedstock may alternatively be at least in part derived from oligomerization or alkylation reactions. Such paraffinic feedstock mixture preparation methods are inherently imprecise and produce a mixture of compounds. The paraffinic feedstock mixtures to the dehydrogenation process may contain quantities of paraffins having multiple branches and paraffins having multiple carbon atoms in the branches, cycloparaffins, branched cycloparaffins, or other compounds having boiling points relatively close to the desired compound isomer. Thus, the paraffinic feedstock mixtures to the dehydrogenation step can also contain sizable quantities of aromatic hydrocarbons.

Another source of paraffins is in condensate from gas wells. Usually insufficient quantities of such condensate are available to be the exclusive source of paraffinic feedstock. However, its use to supplement other paraffinic feedstocks can be desirable. Typically these condensates contain sulfur compounds, which have restricted their use in the past. As the selective hydrogenation process disclosed herein enables the use of sulfur-containing feeds, these condensates can be used to supply paraffins for alkylation.

Paraffins may also be produced from synthesis gas (Syngas), hydrogen and carbon monoxide. This process is generally referred to as the Fischer-Tropsch process. Syngas may be made from various raw materials including natural gas and coal, thus making it an attractive source of paraffinic feedstock where petroleum distillates are not available.

The hydrogenatable hydrocarbon mixture to the selective hydrogenation process disclosed herein should be sufficiently free of impurities, such as water, nitrogen compounds and sulfur compounds, that can unduly adversely affect the life of the selective hydrogenation catalyst. However, it is within the scope of the process disclosed herein to allow or to introduce sulfur compounds such as a sulfur-containing organic species in the hydrogenatable hydrocarbon mixture. It is also within the scope of the process disclosed herein to allow or to introduce relatively volatile sulfur compounds such as hydrogen sulfide ($H_2S$) in the hydrogen-containing make-up gas that is mixed with the hydrogenatable hydrocarbon mixture and passed to the selective hydrogenation catalyst. Without being bound to a particular theory, it is believed that such methods of subjecting the catalyst to the presence of sulfur modify the catalytic performance of the selective hydrogenation catalyst.

The hydrogenatable hydrocarbon mixture may also contain aromatic byproducts produced by dehydrogenation of the paraffinic feedstock, as described in U.S. Pat. No. 5,276,231. Alternatively, the selective aromatics removal process described in U.S. Pat. No. 5,276,231 may be used to remove some or essentially all of the aromatic byproducts upstream of the selective hydrogenation process disclosed herein.

In the selective hydrogenation process disclosed herein, hydrogenatable hydrocarbon mixtures of $C_5$-$C_{11}$ diolefins and $C_5$-$C_{11}$ monoolefins are contacted with the catalyst disclosed herein in a selective hydrogenation zone maintained under selective hydrogenation conditions. This contacting can be accomplished in a fixed catalyst bed system, a moving catalyst bed system, a fluidized bed system, etc., or in a batch-type operation. A fixed bed system is preferred. In this fixed bed system the hydrocarbon feed stream is preheated to the desired reaction temperature and then flowed into the selective hydrogenation zone containing a fixed bed of the catalyst. The selective hydrogenation zone may itself comprise one or more separate reaction zones with temperature regulation means there between to ensure that the desired reaction temperature can be maintained at the entrance to each reaction zone. The hydrocarbon may be contacted with the catalyst bed in either upward, downward or radial flow fashion. Downflow of the hydrocarbon through a fixed catalyst bed is preferred. The catalyst may be in the presence of a liquid phase, and preferably in either an all-liquid phase or at supercritical conditions.

The conditions for carrying out selective hydrogenation processes are well known in the art and can be carried out in a batch type or a continuous type operation. Generally, selective hydrogenation conditions include without limitation pressures of about 0 kpa(g) (0 psi(g)) to about 6894 kPa(g) (1000 psi(g)), temperatures of between 30° C. (86° F.) and 300° C. (572° F.), $H_2$ to diolefin mole ratios of about 0.1:1 to about 10:1, preferably about 1.1:1 to about 1.5:1 and/or a hydrogen to total liquid feed molar ratio of about 0.1:1 to 20:1 and liquid hourly space velocities (LHSV) of about 0.5 to about 30 $hr^{-1}$. It is recognized that achieving conditions where the lower $H_2$ to diunsaturate mole ratios is less than about 1:1 would only be desirable if the conversion needed to be limited. As used herein, diunsaturate includes both diolefinic compounds and compounds having a triple bond. As used herein, the abbreviation "LHSV" means liquid hourly space velocity, which is defined as the volumetric flow rate of liquid per hour divided by the catalyst volume, where the liquid volume and the catalyst volume are in the same volumetric units.

The effluent stream from the selective hydrogenation zone generally will contain unconverted hydrogenatable hydrocarbons, hydrogen and the products of hydrogenation reactions. This effluent stream may be cooled and passed to a hydrogen separation zone to separate a hydrogen-rich vapor phase from a hydrocarbon-rich liquid phase. A separate hydrogen separation zone may not be needed where the $H_2$ to diunsaturate mole ratio is near to 1:1. The hydrocarbon-rich liquid phase, or the effluent stream in the absence of a separate hydrogen separation zone, is separated by means of either a suitable selective adsorbent, a selective solvent, a selective reaction or reactions or by means of a suitable fractionation scheme. Unconverted hydrogenatable hydrocarbons are recovered and may be recycled to the selective hydrogenation zone. The $C_5$-$C_{11}$ monoolefin products of the hydrogenation reactions are recovered as final products or as intermediate products in the preparation of other compounds.

The hydrogenatable hydrocarbons usually do not need to be admixed with a diluent material before, while or after being flowed to the selective hydrogenation zone. The selective hydrogenation reactions of the diunsaturates to monounsaturates are considered to be moderately exothermic, and the temperature rise in the selective hydrogenation reactor is typically not excessive. The selective hydrogenation reactor preferably does not have indirect heat exchange means to remove the heat as it is produced and the reactor may be adiabatic. If used, the diluent material may be hydrogen or a paraffin having from 8 to 19 carbon atoms per molecule. Any diluent passed to the selective hydrogenation zone will typically be separated from the effluent and recycled to the selective hydrogenation reaction zone.

All references herein to the groups of elements of the periodic table are to the IUPAC "New Notation" as shown on the Periodic Table of the Elements in the inside front cover of the book titled CRC Handbook of Chemistry and Physics, ISBN 0-8493-0480-6, CRC Press, Boca Raton, Fla., U.S.A., 80$^{th}$ Edition, 1999-2000.

The following examples are presented in illustration of this invention and are not intended as undue limitations on the generally broad scope of the invention as set out in the appended claims.

ILLUSTRATIVE EMBODIMENT

Comparative Example 1

Catalyst A

Catalyst A was a commercial selective hydrogenation reference catalyst comprising a gamma-alumina support having a 1600 micron diameter and containing 0.4 wt-% Pd and 0.6 wt-% Li.

Example 1

Catalyst B

A catalyst of the invention was prepared by applying a 100 micron outer layer of gamma-alumina to a cordierite sphere having a nominal diameter of 1600 microns. The layered sphere was impregnated with metals, then calcined, and then reduced. The following metal loadings based on the weight of the catalyst were achieved: 0.1 wt-% Pd, 0.19 wt-% Cu, and 0.4 wt-% K.

Example 2

Catalyst C

A catalyst of the invention was prepared by applying a 100 micron outer layer of gamma-alumina to a cordierite sphere having a nominal diameter of 1600 microns. The layered sphere was impregnated with metals, then calcined, and then reduced. The following metal loadings based on the weight of the catalyst were achieved: 0.1 wt-% Pd and 0.125 wt-% Li.

Example 3

Catalyst D

A catalyst of the invention was prepared by applying a 100 micron outer layer of gamma-alumina to a cordierite sphere having a nominal diameter of 1600 microns. The layered sphere was impregnated with metals, then calcined, and then reduced. The following metal loadings based on the weight of the catalyst were achieved: 0.2 wt-% Pd and 0.125 wt-% Li.

Example 4

Catalyst E

A catalyst of the invention was prepared by applying a 200 micron outer layer of gamma-alumina to a cordierite sphere having a nominal diameter of 1600 microns. The layered sphere was impregnated with metals, then calcined, and then reduced. The following metal loadings based on the weight of the catalyst were achieved: 0.2 wt-% Pd and 0.25 wt-% Li.

Example 5

The diolefin conversion and selectivity of the catalysts prepared in Examples 1 to 4 were studied using a blended feed prepared from a simulated product of a commercial pyrolysis gasoline (pygas) unit. A volume of the catalyst to be tested was loaded in a reactor, and the blended feed flow was started under selective hydrogenation conditions. Throughout the test, the pressure was maintained at approximately 3447 kpa (g) (500 psi(g)), the LHSV was maintained approximately constant except as indicated in Table 4, and a liquid phase was present. The catalyst was evaluated and the product was sampled while the average bed temperature was adjusted over a range of from about 50° C. (122° F.) to about 120° C. (248° F.). The average bed temperature was computed to be the arithmetic average of four catalyst bed temperatures at locations spaced uniformly along the length of the bed. The molar ratio of hydrogen to hydrocarbon ($H_2$/HC) in the blended feed was maintained approximately constant at about 2.5:1, except as indicated in Table 4. Under these conditions, the molar ratio of hydrogen to diolefin in the blended feed was greater than 5:1. A molar excess of hydrogen relative to hydrocarbon or to diolefin favors the promotion of the unwanted olefin saturation reactions, which makes the selective conversion of the diolefin to the desired monoolefin even more difficult. The evaluation of the catalyst indicated that the results remained relatively constant with time on stream after the catalyst passed the initial period after a change in test conditions.

A fresh feedstock with a typical pygas unit product composition was prepared by blending individual hydrocarbon components to evaluate the prepared catalysts. The composition of the fresh feedstock is given in Table 1. For purposes of these examples, the hydrocarbon components are categorized by hydrocarbon species as Saturates, Olefins, Diolefins, and Aromatics.

TABLE 1

Composition of Fresh Feedstock

| Component | Hydrocarbon Species | Concentration, wt-% |
|---|---|---|
| n-Pentane | Saturate | 5.12 |
| Cyclopentane | Saturate | 0.84 |
| 1-Pentene | Olefin | 2.52 |
| 1,3-Pentadiene | Diolefin | 7.29 |
| Cyclopentene | Olefin | 0.75 |
| Cyclohexane | Saturate | 1.31 |
| 1-Hexene | Olefin | 0.66 |
| 1,5-Hexadiene | Diolefin | 3.3 |
| 1,4-Cyclohexadiene | Diolefin | 2.75 |
| Benzene | Aromatic | 32 |
| Cycloheptane | Saturate | 0.37 |
| 1-Heptene | Olefin | 0.16 |
| Toluene | Aromatic | 17.5 |
| n-Octane | Saturate | 0.05 |
| Cyclooctane | Saturate | 0.05 |
| 1-Octene | Olefin | 0.13 |
| 1,7-Octadiene | Diolefin | 1.45 |
| EthylBenzene | Aromatic | 0.75 |
| Styrene | Olefin | 5.33 |
| p-Xylene | Aromatic | 1.39 |
| m-Xylene | Aromatic | 3.46 |
| o-Xylene | Aromatic | 2.15 |
| 1,3,5-TriMethylBenzene | Aromatic | 0.47 |
| alpha-MethylStyrene | Olefin | 0.56 |
| Indene | Olefin | 1.78 |
| Indan | Aromatic | 0.19 |
| t-ButylBenzene | Aromatic | 1.81 |
| Dicyclopentadiene | Diolefin | 5.87 |
| Total | | 100 |

The composition of the fresh feedstock by hydrocarbon species is given in Table 2. The fresh feedstock contains $C_5$-$C_{10}$ Diolefins, Olefins, Aromatics, and Saturates that are commonly found in cracker derived gasoline streams.

TABLE 2

Composition of Fresh Feedstock by Hydrocarbon Species

| Hydrocarbon Species | Concentration, wt-% |
|---|---|
| Saturates | 7.7 |
| Aromatics | 59.7 |
| Olefins | 11.9 |
| Diolefins | 20.7 |
| Total | 100 |

The invention discloses catalysts that selectively convert the diolefins almost to extinction and preferably to olefins, while converting some and preferably few of the olefins in the feed to the corresponding saturate and while maintaining the aromatic components in the feed without conversion.

The fresh feedstock given in Tables 1 and 2 was blended in equal proportions with a diluent containing aromatics and saturates to provide a heat sink and simulate a recycle stream of a selective hydrogenation process. The combined feed after the blending is given in Table 3.

TABLE 3

Composition of the Blended Feed by Hydrocarbon Species (50% Diluent and 50% Fresh Feedstock)

| Hydrocarbon Species | Concentration, wt-% |
|---|---|
| Saturates | 7.9 |
| Aromatics | 75.9 |
| Olefins | 5.9 |
| Diolefins | 10.3 |
| Total | 100 |

A sulfur-containing compound was also added to the blended feed in an amount that resulted in a concentration of 30 wt-ppm sulfur in the blended feed, to simulate the high sulfur content expected in gasoline streams derived from thermal or catalytic crackers.

The results obtained are illustrated in FIGS. 1 to 4. Prior to discussing the results in detail, two general observations should be made with respect to FIGS. 1 to 4. First, while all tested catalysts tend to show increased diolefin conversion as the average bed temperature increases, superior catalysts show high diolefin conversion at relatively low average bed temperature. Second, while all tested catalysts tend to show decreased selectivity in converting diolefins to monoolefins as the diolefin conversion increases, superior catalysts show high selectivity to monoolefins while at high diolefin conversion.

FIG. 1 illustrates the activity of Catalysts A through E in converting $C_5$ diolefin, i.e. pentadiene. Layered sphere Catalysts B, C, and D each had better activity (i.e. showed higher conversion) than Catalyst A at an average bed temperature of 50° C. (122° F.), despite the active metal loadings of Catalysts B, C, and D being between one-fourth and one-half of the active metal loading of Catalyst A. At the higher bed temperatures of 85° C. (185° F.) and 120° C. (248° F.), layered Catalyst E had the highest $C_5$ diolefin conversion (essentially 100%) of all the tested catalysts, despite Catalyst E having an active metal loading one-half that of Catalyst A. Although the observed differences in the activities of the layered and non-layered catalysts are relatively small due to the elevated bed temperatures, the other layered Catalysts B, C, and D all showed $C_5$ diolefin conversions that are above 90% and thus in the same $C_5$ diolefin conversion range as Catalyst A at these elevated temperatures.

Figure 2:
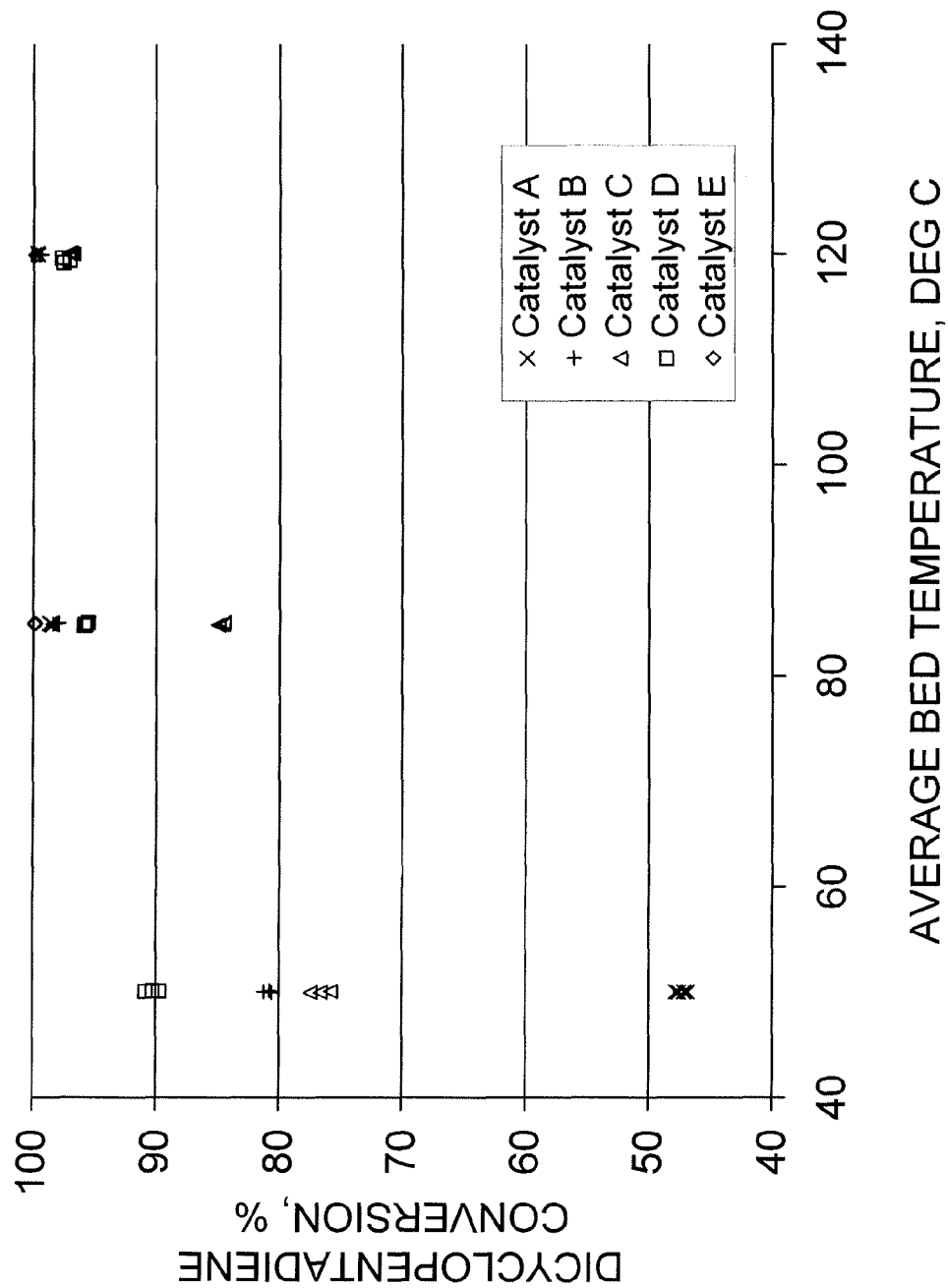
FIG. 2 compares the activities of different catalysts A, B, C, D and E in a plot of the percentage of dicyclopentadiene conversion against the average bed temperature of the catalyst bed.

FIG. 2 depicts the activity of Catalysts A through E for converting the $C_{10}$ diolefin component, i.e. dicyclopentadiene. FIG. 2 also shows that layered sphere catalysts B, C and D each had higher activity than Catalyst A at an average bed temperature of 50° C. (122° F.). At the higher bed temperatures of 85° C. (185° F.) and 120° C. (248° F.), layered Catalyst E had the highest $C_5$ diolefin conversion (100%) of all the tested catalysts. Except for the relatively low conversion of Catalyst C at 85° C. (185° F.), the observed differences in the activities of the layered and non-layered catalysts are relatively small due to the elevated bed temperatures. Layered Catalysts B, C, and D all showed $C_5$ diolefin conversions that are above 95% and in the same $C_5$ diolefin conversion range as Catalyst A.

In summary, FIGS. 1 and 2 show that layered Catalysts B, C, D and E, each having a significant benefit in terms of decreased active metal loading compared to Catalyst A, show activities for $C_5$ and $C_{10}$ diolefin conversion that are better than, the same as, or at least not significantly worse than those of Catalyst A. Similar activity comparisons for the conversions of $C_6$, $C_7$, and $C_8$ diolefins by Catalysts A through E were observed.

Figure 3:
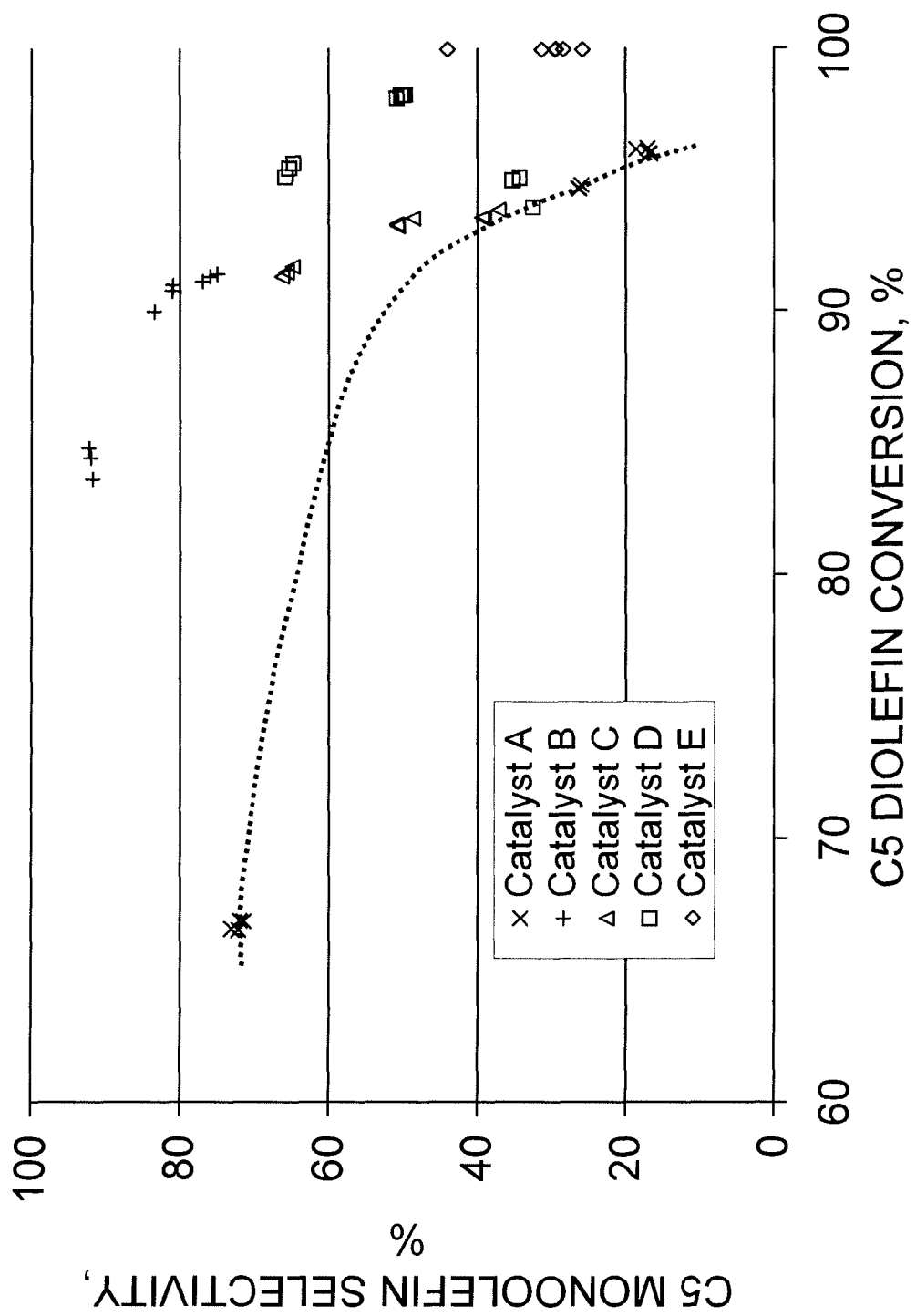
FIG. 3 compares the selectivities of different catalysts A, B, C, D and E in a plot of the percentage of selectivity to $C_5$ monoolefins against the percentage of $C_5$ diolefin conversion.
Figure 4:
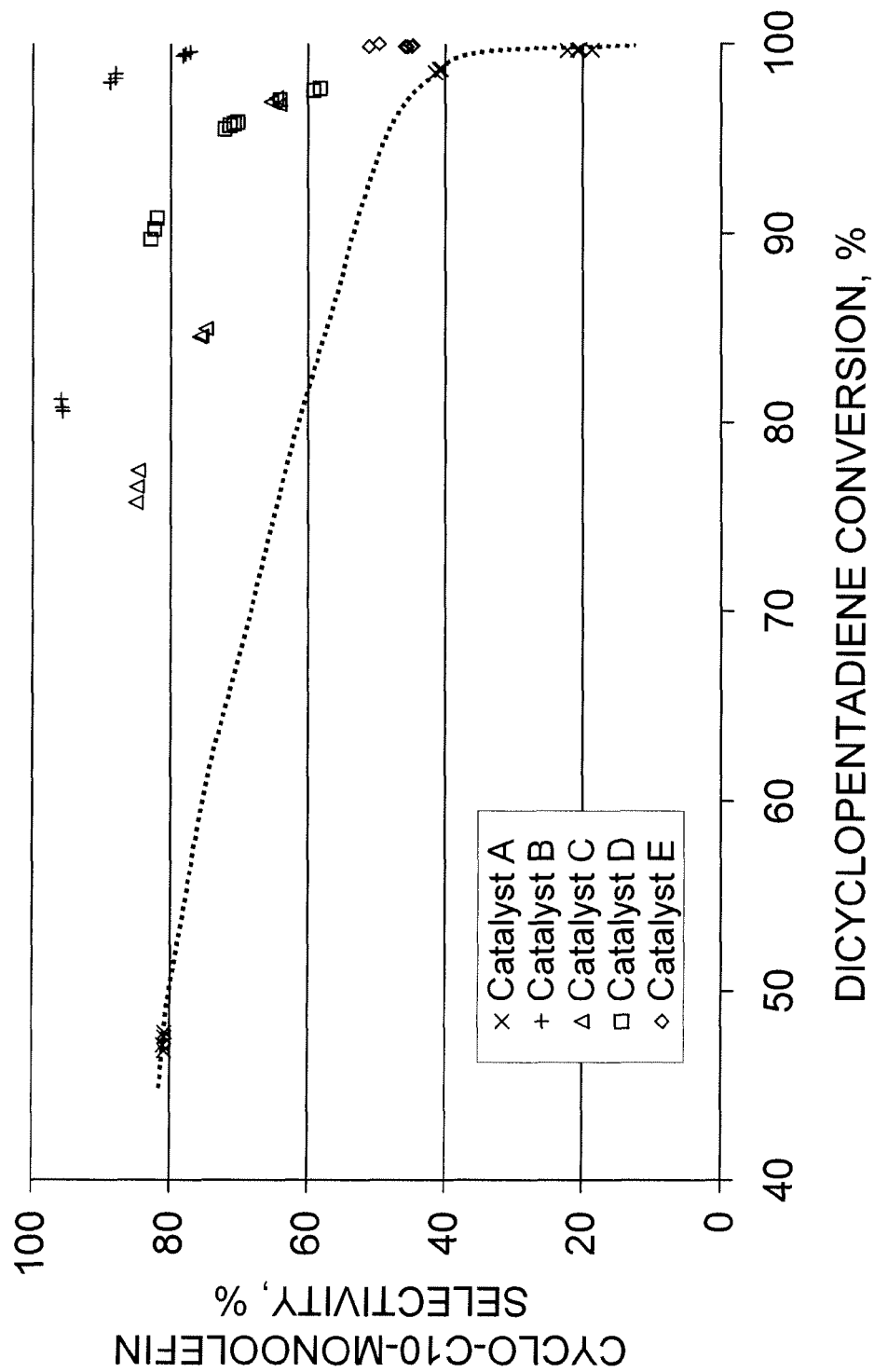
FIG. 4 compares the selectivities of different catalysts A, B, C, D and E in a plot of the percentage of dicyclopentadiene selectivity to cyclo-$C_{10}$-monoolefin against the percentage conversion of dicyclopentadiene.

FIGS. 3 and 4 illustrate that layered sphere Catalysts B, C, D and E all have better selectivities to monoolefins when converting diolefins in comparison to Catalyst A. The selectivities were calculated by a carbon number and species identification. In FIG. 3, the selectivity was calculated to be 100 times the ratio of the amount of $C_5$ monoolefins in the product to the sum of the amount of $C_5$ monoolefins in the feed plus the amount of $C_5$ diolefins converted, where the amount of $C_5$ diolefins converted is the difference of the amount of $C_5$ diolefins in the feed minus the amount of $C_5$ diolefins in the product. The dashed curve in FIG. 3 depicts the expected performance of Catalyst A based on the observed data, and FIG. 3 shows that Catalyst A had the highest propensity to convert the $C_5$ diolefins to the undesired corresponding $C_5$ paraffins. Specifically, Catalyst A converted about 75 to 85% of the total available $C_5$ olefins (i.e., $C_5$ monoolefins and $C_5$ diolefins in the feed) to $C_5$ paraffin at about 95 to 96% $C_5$ diolefin conversion, which is the highest $C_5$ diolefin conversion observed for Catalyst A. In other words, Catalyst A retained only about 15 to 25% of the total available $C_5$ olefins. In contrast, Catalyst D at its highest observed $C_5$ diolefin conversion of about 98% converted only about 50% of the total available $C_5$ olefins to the undesired $C_5$ paraffins, and in the range of about 94 to 98% observed $C_5$ diolefin conversions and despite the range of observed $C_5$ monoolefin selectivities Catalyst D converted at most 70% of the total available $C_5$ olefins to the undesired $C_5$ paraffins.

FIG. 4 shows the selectivity for the conversion of dicyclopentadiene, a $C_{10}$ diolefin, to cyclo-$C_{10}$-monoolefins. The selectivity was calculated in the same manner as described for the selectivity in FIG. 3, except for $C_{10}$ olefins. The dashed curve in FIG. 4 depicts the expected performance of Catalyst A based on the observed data, and Catalyst A converted about 80% of the total available cyclo-$C_{10}$-olefins (i.e., cyclo-$C_{10}$-monoolefins and cyclo-$C_{10}$-diolefins in the feed) to the undesired fully saturated $C_{10}$ naphthenes. In contrast, layered sphere Catalysts B, C, D and E all converted much less of the total available cyclo-$C_{10}$-olefins to $C_{10}$ naphthenes and had much higher selectivity to the corresponding cyclo-$C_{10}$-monoolefin at the same dicyclopentadiene conversion. Specifically, at about 99 to 100% dicyclopentadiene conversion, Catalyst B showed nearly 80% selectivity to the cyclo-$C_{10}$-monoolefin while Catalyst A showed only 20% selectivity to the cyclo-$C_{10}$-monoolefin and thus Catalyst A converted about 80% of the total available cyclo-$C_{10}$-olefins to the undesired $C_{10}$ naphthenes.

In summary, FIGS. 3 and 4 show that layered Catalysts B, C, D and E show selectivities for $C_5$ and $C_{10}$ monoolefins that are about the same as or better than those of Catalyst A. It can be seen from FIGS. 1-4 that the invention provides the ability to selectively convert diolefins to olefins while having a reduced tendency to saturate the monoolefins.

Table 4 shows the aromatic component retention in weight % during a test of Catalyst D. The weight % aromatic retention is calculated as 100 times the ratio of the amount of aromatic species found in the product to that found in the feed. For the aromatic species in the blended feed, specifically benzene, toluene, xylene, and butylbenzene, the aromatic retention is preferably at 100%. Catalyst D shows, at the base conditions including the lowest average bed temperature, over 95% retention of each of the four aromatic species. Relative to the base conditions, a 35° C. (63° F.) higher average bed temperature, a 5% lower LHSV, and a 6% higher $H_2$/HC result in less than 1% change in the aromatic retentions. At more severe conditions of a 69° C. (124° F.) higher average bed temperature, a 6% lower LHSV, and a 6% higher $H_2$/HC, each aromatic retention falls by from 1 to 7% below its respective base aromatic retention, with the benzene retention falling the most. All the aromatic retentions, including that of benzene, are restored to within 1% of their base aromatic retentions at nearly the same average bed temperature (70° C. (126° F.) above the base) by increasing the LHSV to 31% above the LHSV base, even though the $H_2$/HC is 14% higher than the $H_2$/HC base.

TABLE 4

| Time on Stream, hours | 14 | 22 | 27 | 41 |
|---|---|---|---|---|
| Average Bed Temperature, ° C. | Base | Base + 35 | Base + 69 | Base + 70 |
| Reactor Pressure | Base | 1.00 × Base | 0.98 × Base | 1.00 × Base |
| LHSV | Base | 0.95 × Base | 0.94 × Base | 1.31 × Base |
| H2/HC, mol/mol | Base | 1.06 × Base | 1.06 × Base | 1.14 × Base |
| Aromatic Retention, wt-% | | | | |
| Benzene | Base | 0.99 × Base | 0.93 × Base | 1.00 × Base |
| Toluene | Base | 1.00 × Base | 0.99 × Base | 1.00 × Base |
| Xylenes | Base | 1.00 × Base | 0.99 × Base | 1.01 × Base |
| Butylbenzene | Base | 1.00 × Base | 0.98 × Base | 1.00 × Base |

Example 6

The catalysts were further studied using desorption and adsorption techniques to determine the pore size distribution, the average pore radius, the surface area and the total pore volume of the catalyst. The results of the studies are shown in Table 5.

TABLE 5

| Catalyst | Example 1 - Catalyst B | Example 2 - Catalyst C | Example 3 - Catalyst D | Example 4 - Catalyst E |
|---|---|---|---|---|
| Description | 0.1 wt-% Pd/ 0.19 wt-% Cu/ 0.4 wt-% K | 0.1 wt-% Pd/ 0.125 wt-% Li | 0.2 wt-% Pd/ 0.125 wt-% Li | 0.2 wt-% Pd/ 0.25 wt-% Li |
| Layer Thickness, microns | 100 | 100 | 100 | 200 |
| BET Surface Area, m$^2$/g | 32 | 35 | 32 | 57 |
| Total Pore Volume, cc/g | 0.13 | 0.15 | 0.14 | 0.25 |
| Average Pore Radius, Angstroms | 82 | 84 | 88 | 88 |
| Pore Radius Size Distribution, Angstroms | 10-232 | 10-266 | 10-240 | 10-244 |

The results shown in Table 5 demonstrate that the properties of the catalyst are primarily determined by the layer, which can be relatively carefully controlled and that the core contributes very little to the surface area or pore volume. Thus the core primarily defines the bulk properties of the catalyst that affect, for example, pressure drop, since the bulk fluid mechanical properties are relatively more dependent on the gross parameters of the catalyst and relatively less dependent on the fine details of layer thickness. The composition of the core is primarily important as to inertness to reaction while showing good bonding to the layer. Thus it is possible to relatively independently control both the bulk and microscopic properties of the catalyst.

Figure 5:
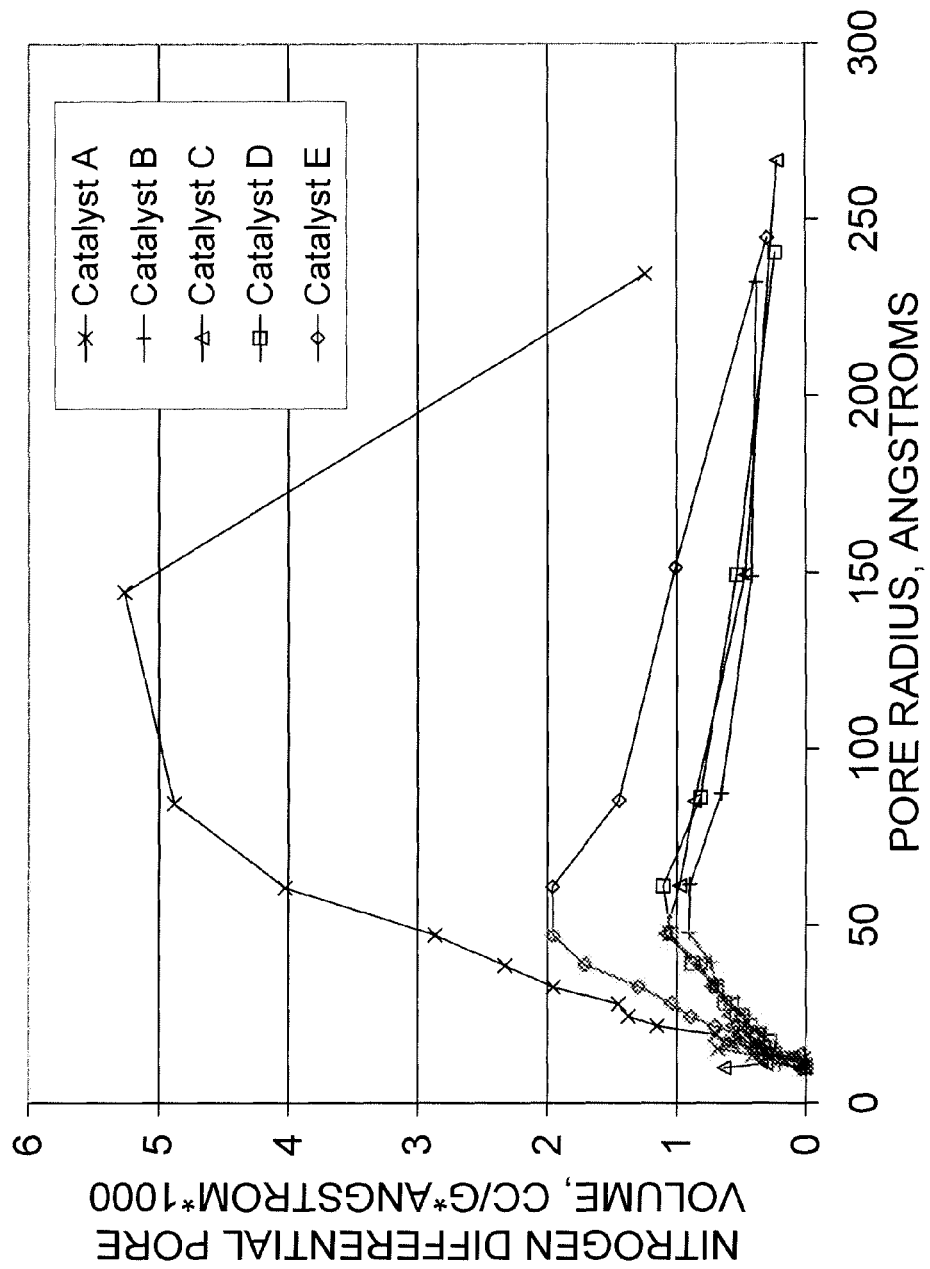
FIG. 5 compares different catalysts A, B, C, D and E in a plot of nitrogen differential pore volumes against the pore radius.
Figure 6:
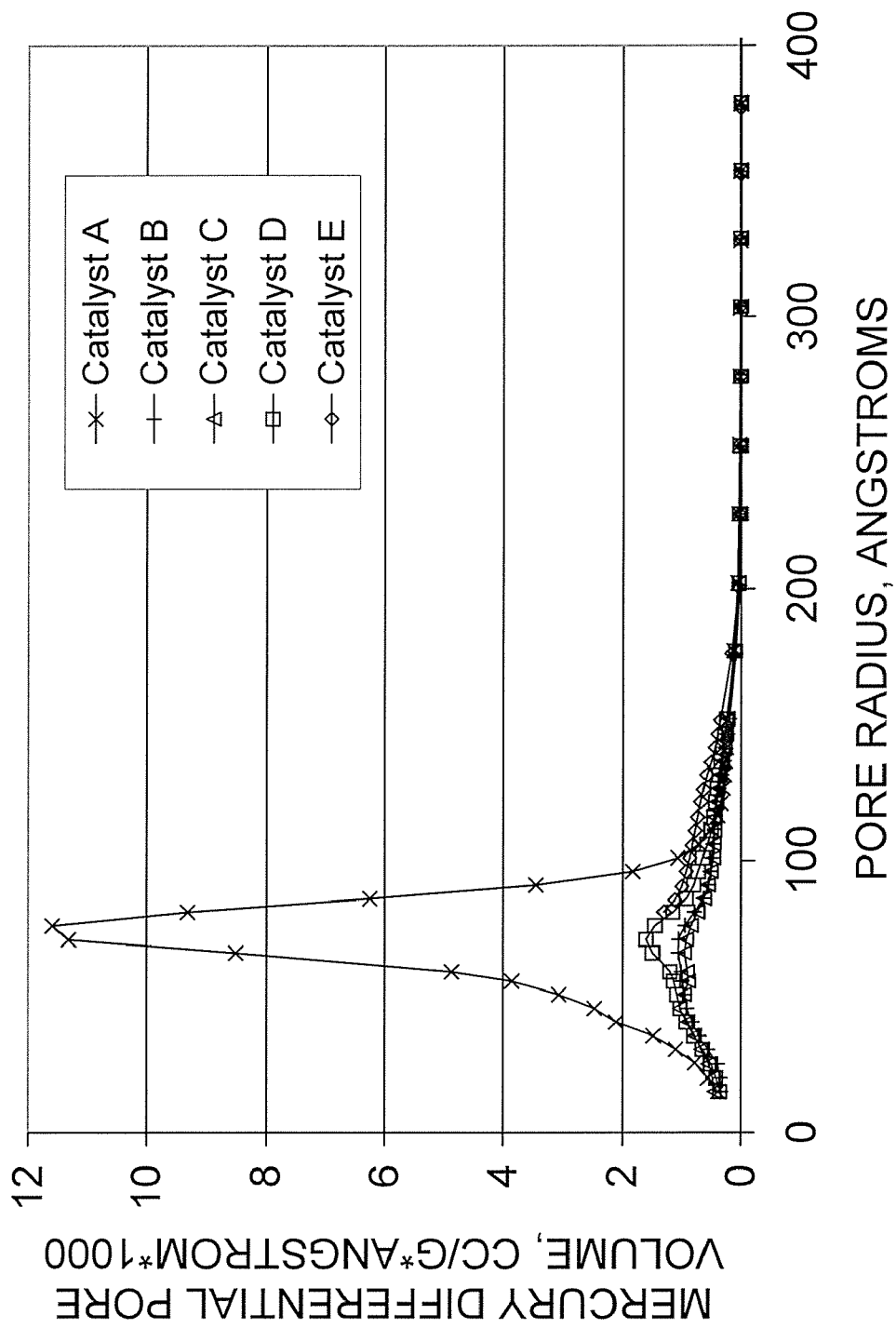
FIG. 6 compares different catalysts A, B, C, D and E in a plot of mercury differential pore volumes against the pore radius.

FIGS. 5 and 6 depict the profiles of the differential pore volume distribution plotted against the pore radius of Catalysts A, B, C, D and E. FIG. 5 depicts the differential pore volume measured using the nitrogen adsorption/desorption method, which is used for pores with a pore radius of from about 10 to about 300 Angstroms. FIG. 6 depicts the differential pore volume measured using the mercury penetration method, which is used for larger pores too. It is believed that the nitrogen adsorption/desorption method is more accurate for determining the differential pore volume for pores below 300 Angstroms. Although there is a difference in the absolute values of the differential pore volume measured for Catalyst A by the two methods in the overlapping region, there is general agreement in the shapes of the profiles. Catalysts B, C, D and E exhibit a maximum nitrogen differential pore volume of about 2 cc/g*Angstrom*1000 at a pore radius 50 to 70 Angstroms. None of the catalysts exhibit significant differential pore volume in pores larger than 300 Angstroms by either the nitrogen adsorption/desorption method or the mercury penetration method.

The invention claimed is:

1. A process for selectively hydrogenating one or more $C_5$-$C_{11}$ diolefins in a hydrocarbon mixture having 0.5 mol% or greater total monolefin content and 0.1 mol% or greater total diolefin content to one or more respective $C_5$-$C_{11}$ monoolefins the process comprising the step of:
   (i) bringing the hydrocarbon mixture under selective hydrogenation conditions into contact with a layered catalyst composition to give substantially a $C_5$-$C_{11}$ monoolefin product; wherein the layered catalyst composition comprises:
      (a) a refractory inner core having an inner core surface area and comprising at least one refractory material, and
      (b) a non-refractory outer layer having an outer layer surface area and bonded to said refractory inner core, said non-refractory outer layer comprising at least one non-refractory material and has dispersed thereon at least one IUPAC Group 1-2 metal and at least one IUPAC Group 8-10 metal;
   (ii) wherein a predetermined efficacy of the layered catalyst composition for selectively hydrogenating one or more $C_5$-$C_{11}$ diolefins in the hydrocarbon mixture is obtained, whereby the selectivity for conversion of dicyclopentadiene (DCPD) to its corresponding cyclo-$C_{10}$-monoolefin is 55% or greater, as determined at a DCPD conversion of 95%, and
      (a) said predetermined efficacy is determined by a selective hydrogenation testing procedure, wherein a hydrocarbon testing mixture, having 5.9 wt% monoolefins, 2.9 wt% dicyclopentadiene (DCPD), 7.4 wt% non-DCPD diolefins, 7.9 wt% saturated hydrocarbons and 75.9 wt% aromatics, is treated with said layered catalyst composition under a selective hydrogenation process (SHP) test conducted at 3447 kPa(g) over a temperature range from 50° C. to 120° C., using a hydrogen to total hydrocarbon molar ratio of 2.5:1 and a liquid hourly space velocity (LHSV) of 3 hr$^{-1}$.

2. The process as claimed in claim 1 wherein the selective hydrogenation conditions include a temperature of about 30° C. to about 300° C.

3. The process of claim 1 wherein the selective hydrogenation conditions includes a hydrogen to diolefin molar ratio of about 1:1 to 10:1 and/or a hydrogen to total liquid feed molar ratio of about 0.1:1 to 20:1.

4. The process as claimed in claim 1 wherein between 30 to 80% of the one or more C5-C11 diolefins are selectively hydrogenated to the one or more respective C5-C11monoolefin products.

5. The process of claim 1 further characterized in that the catalyst is prepared by a method comprising depositing the at least one IUPAC Group 1-2 metal and at least one IUPAC Group 8-10 metal on the non-refractory material after the non-refractory outer layer is bonded to the refractory inner core.

6. The process of claim 5 further characterized in that the non-refractory outer layer is in the presence of a liquid phase during the deposition of the at least one IUPAC Group 1-2 metal and the at least one IUPAC Group 8-10 metal onto the non-refractory material.

7. The process of claim 1 further characterized in that the non-refractory outer layer is modified by a hydrothermal treatment process to obtain a predetermined pore size.

8. The process of claim 1 wherein the refractory material is selected from the group consisting of alpha alumina, silicon carbide, refractory metals, cordierite, and mixtures thereof.

9. The process of claim 1 wherein the refractory inner core is cordierite.

10. The process of claim 1 wherein the non-refractory material is selected from the group consisting of gamma alumina, delta alumina, eta alumina, theta alumina, silica/alumina, zeolites, nonzeolitic molecular sieves, titania, zirconia, hydrotalcite, non-refractory metals and mixtures thereof.

11. The process of claim 1 wherein the non-refractory outer layer is gamma alumina.

12. The process of claim 1 wherein the at least one IUPAC Group 1-2 metal is a metal selected from the group consisting of potassium, lithium, and mixtures thereof.

13. The process of claim 1 wherein the at least one IUPAC Group 8-10 metal is a metal selected from the group consisting of platinum and palladium.

14. The process of claim 1 wherein the non-refractory material has further dispersed thereon one or more IUPAC Group 11-17 metals.

15. The process of claim 14 wherein the one or more IUPAC Group 11-17 metal is selected from the group consisting of copper, silver, gold, tin, germanium, lead and mixtures thereof.

16. The process of claim 1 wherein the non-refractory outer layer has a thickness of from about 1 micron to about 300 microns.

17. The process of claim 1 wherein the non-refractory outer layer of the catalyst has a surface area of about 5 m2/g to about 1000 m2/g based on the weight of the non-refractory outer layer and the refractory inner core surface area is less than the non-refractory outer layer surface area wherein the refractory inner core has a substantially lower adsorptive capacity for catalytic metal precursors relative to the non-refractory outer layer.

18. The process of claim 1 wherein the layered catalyst composition is prepared by a process comprising:
  i) coating the refractory inner core with a slurry comprising the non-refractory material, to obtain a coated refractory inner core, depositing on the coated refractory inner core at least one IUPAC Group 1-2 metal and at least one IUPAC Group 8-10 metal in the presence of a second liquid phase, drying the coated refractory inner core and calcining at a temperature of about 400° C. to about 900° C. for a time sufficient to bond the non-refractory outer layer to the refractory inner core and provide a layered support; and
  ii) reducing the product of step i) under reduction conditions to provide the layered catalyst composition.

* * * * *